United States Patent [19]
Hughes

[11] Patent Number: 6,058,932
[45] Date of Patent: *May 9, 2000

[54] ACOUSTIC TRANSCEIVER RESPIRATORY THERAPY APPARATUS

[76] Inventor: Arthur R. Hughes, 11990 Meadowood La., Parker, Colo. 80138

[*] Notice: This patent is subject to a terminal disclaimer.

[21] Appl. No.: 09/248,913

[22] Filed: Feb. 9, 1999

Related U.S. Application Data

[63] Continuation-in-part of application No. 09/096,878, Jun. 12, 1998, Pat. No. 5,893,361, which is a continuation-in-part of application No. 08/843,745, Apr. 21, 1997, Pat. No. 5,829,429.

[51] Int. Cl.$^7$ ................................................. A61M 15/00
[52] U.S. Cl. .......................... 128/200.24; 601/41; 482/13
[58] Field of Search ........................ 128/200.24, 202.28, 128/202.29, 205.12; 601/41, 43; 482/13

[56] References Cited

U.S. PATENT DOCUMENTS

| | | | |
|---|---|---|---|
| 2,918,917 | 12/1959 | Emerson | 601/41 |
| 5,451,190 | 9/1995 | Liardet | 482/13 |
| 5,829,429 | 11/1998 | Hughes | 128/200.24 |

*Primary Examiner*—Aaron J. Lewis
*Attorney, Agent, or Firm*—John R. Wahl

[57] ABSTRACT

An active respiratory therapeutic device and method for actively loosening and breaking up mucus plugs and phlegm in a user's trachea and bronchial passages and lungs while a user is breathing normally through the device comprises a housing containing a base portion and a cap portion forming at least a portion of a sonic coupling chamber adapted to be held in a patient's mouth during normal breathing activity. The cap portion also includes breathing passages out of the chamber so that the user can breath normally through device during operation. The base portion contains an acoustic generator, preferably behind a sanitary flexible diaphragm separating the portions. The portions may be separately housed and connected electrically. The acoustic generator produces an audio waveform which may be controlled by the user or automatically controlled by a feedback signal to optimize a sensed parameter indicative of the user's breathing efficiency such as the sound of the user's exhaled breath, blood oxygen levels, or ultrasonic signature changes of mucus plugs. This feedback signal senses a patient parameter and automatically adjust the operating frequency spectrum and/or pulse rate of the device to optimally affect the monitored parameter such as the user's breathing efficiency. The method of the invention basically comprises determining a resonant frequency of a mucus plug, generating an acoustic waveform including the resonant frequency and directing the waveform into a user's airways to loosen the plug while the user breathes through his or her airways. Alternative embodiments include ports for introduction of medicinal agents into the breathing passages during operation and separate modules, such as a separate power supply module connected to a transducer/face mask module to couple the acoustic generator into a patients airways for use with unconscious patients or neonatal patients.

29 Claims, 8 Drawing Sheets

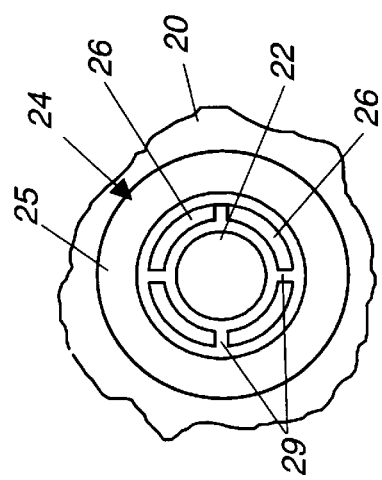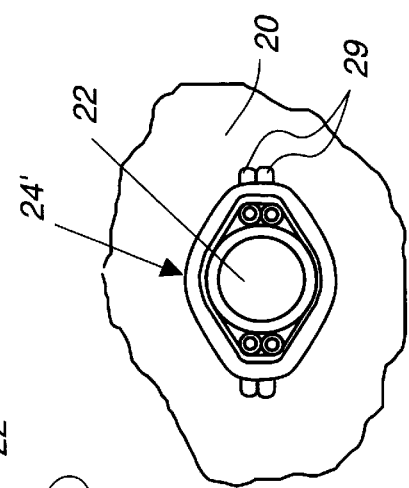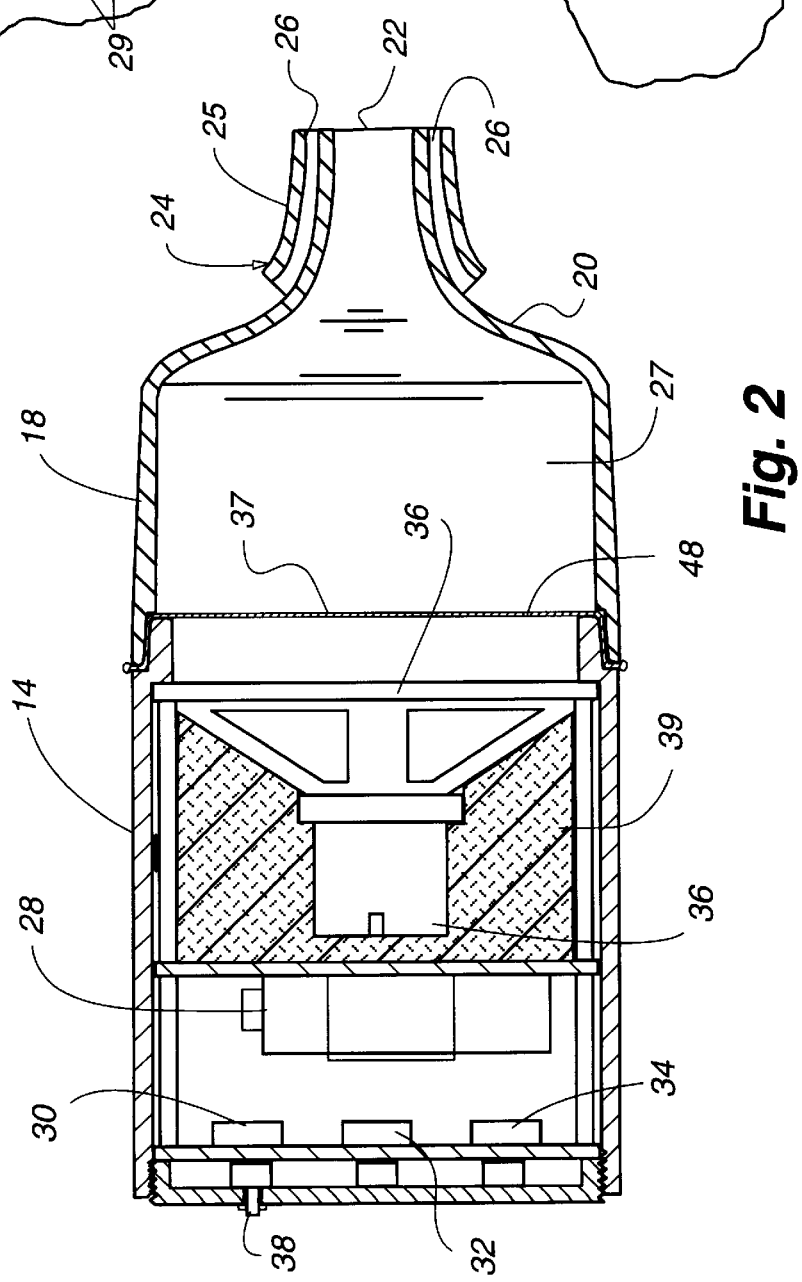

ACOUSTIC TRANSCEIVER RESPIRATORY THERAPY APPARATUS

CROSS REFERENCE TO RELATED APPLICATIONS

This application is a continuation in part of U.S. patent application Ser. No. 09/096,878 filed on Jun. 12, 1998, now U.S. Pat. No. 5,893,361, entitled ACOUSTIC TRANSCEIVER RESPIRATORY THERAPY APPARATUS AND METHOD, which is a continuation in part of U.S. patent application Ser. No. 08/843,745, filed Apr. 21, 1997 entitled ACOUSTIC RESPIRATORY THERAPY APPARATUS, now U.S. Pat. No. 5,829,429, issued Nov. 3, 1998.

BACKGROUND OF THE INVENTION

1. Field of the Invention

This invention generally relates to respiratory devices and more particularly to a vibrating device and method which assists in breaking up and dislodging accumulated fluids and solids generated in a user's lungs.

2. Description of the Related Art

People who have lung diseases such as cystic fibrosis, bronchiactasis and chronic bronchitis have a difficult time breaking up, dislodging, and expelling mucus and phlegm which develops in the lungs. The presence of this material in the lungs and bronchial and tracheal passages provides an excellent media for growth of bacteria. For treatment of the condition, rotation of antibiotics is used to treat the bacterial infections that result. Postural drainage with induced vibration , percussive therapy and/or the use of a mechanical device such as a flutter valve are often used to help the patient dislodge this mucus material.

Such percussive devices are disclosed in U.S. Pat. Nos. 5,018,517 and 5,451,190 to Liardet. This device is self powered, as are other flutter valve devices available and in use today. That is, the patient exhales into the device which sets up vibrations which feed back through the patient's air ways to break up and dislodge the phlegm. However, this activity is energy consumptive and very draining to the patient. Often, because of a debilitating condition from the effects of pneumonia, for example, the patient has great difficulty blowing into these self powered mechanical devices with sufficient force to achieve any substantive success at dislodging accumulated phlegm.

An active vibratory device is disclosed in U.S. Pat. No. 4,813,403 to Endo. This device comprises an oscillator for generating an electrical signal at a frequency optimally effective for the patient, an audio amplifier, and a transducer connected, through a closed gas volume, to a vibratory diaphragm which is placed against the patient's body, typically the patient's chest or back. The vibration is then transferred from the transducer, through the closed gas volume, to the diaphragm, then to the surface of the patient's body to treat such problems as shoulder discomfort, arthritis, asthmatic spasms and improve blood circulation. The major disadvantage with this approach when the lungs are the target is that by placing the unit on a user's back or chest, the intervening body tissue may substantially attenuate the vibration before it reaches the target area of the lungs and bronchial tubes.

Therefore there is an urgent need for a device that can efficiently and effectively transmit acoustic vibrations to the sites of phlegm buildup in the patient's lungs. There is also a need for a device which does not exhaust the patient's energy during device operation so that this energy can be reserved for effective expulsion of dislodged phlegm. There is a further need for a device that permits introduction of pharmacological agents into a patient's airways during operation of a device to assist a patient in dislodging phlegm. There is also a need for a therapeutic phlegm removal device that may be utilized on very small children, babies and in critical care environments.

SUMMARY OF THE INVENTION

The method and apparatus in accordance with the present invention meets the above identified needs.

It is thus an object of the invention to provide a powered apparatus for directly assisting a patient in breaking up phlegm and mucus plugs in the patient's lungs and bronchial tubes while permitting administration of pharmacological agents and aerosol sprays into a patient's airways.

It is another object of the invention to provide a modular powered acoustical apparatus that the patient may adjust to achieve optimal breakup of phlegm and mucus plugs while minimizing the size and mass of the module placed against the patient's mouth.

It is another object of the invention to provide a modular powered acoustical apparatus that a patient may utilize to achieve optimal breakup of phlegm and mucus plugs without generating bothersome sound levels to persons in close proximity to the patient.

It is a still further object of the invention to provide a method for optimal loosening and breakup of phlegm and mucus plugs in a patient's airways and lungs while simultaneously permitting application of pharmaceutical agents into the patient's airways.

It is a still further object of the invention to provide an active acoustical apparatus that can automatically generate an acoustic waveform that approximates the frequency spectrum of a patient's breathing sounds to optimize breakup of phlegm and mucus plugs in the patient's airways.

It is another object of the invention to provide a powered apparatus which a patient can use while breathing in a normal manner and which automatically optimizes transmission of acoustic vibrations directly into a patient's airways based on monitoring of at least one physical parameter indicative of one or more body functions.

These and other objects and features of the invention are achieved by utilizing an electrically powered apparatus which produces an acoustic signal and directs the signal directly into a patient's airways. The acoustic signal may comprise a continuous tonal spectrum or noise spectrum, an intermittent acoustic spectrum, or series of sound pulses, or other modulated or unmodulated acoustic spectrum. The apparatus comprises a housing, either unitary or modular, a power supply, an acoustic generator preferably including a variable frequency oscillator and an audio amplifier in the housing connected to the power supply, an acoustic transducer such as a speaker connected to the amplifier and preferably facing a biologic barrier such as an elastic diaphragm in the housing forming a portion of a sonic coupling air chamber in the housing, and a mouthpiece at one end of the housing connected to the air chamber. The mouthpiece is adapted to be held in a user's mouth while breathing during operation of the apparatus.

When the user closes his or her mouth around the mouthpiece of the apparatus, the mouthpiece forms a passage which directly couples the air chamber into the user's airways including the user's, i.e., patient's, bronchial tubes and lungs. The housing also has a breathing passage or series of ports preferably formed around and alongside the mouthpiece, or alternatively formed by a plurality of small holes through the peripheral wall of the air chamber in the housing. These passages permit the user's breath to exit the sonic coupling air chamber. The user draws fresh air for each breath into his or her lungs during operation of the apparatus through these breathing passages.

The breathing passages may be formed by one or more tubes or tubular passages coaxially extending alongside the central passage through the mouthpiece. These breathing passages may be integrally formed in the mouthpiece by a short annular sleeve formed around the central passage through the mouthpiece. The breathing passages have a total cross sectional area that is much smaller than the central passage through the air chamber and mouthpiece into the user's mouth, bronchial tubes and lungs. However, the breathing passage or passages cross sectional area is large enough to permit the user to breath at a normal rate without undue restriction.

The mouthpiece may also be elongated and include a connection such as a socket with a removable cover to receive a pharmacological agent dispensing device such as an aerosol dispenser, a Nebulizer, a PEP device or other device such that the agent may be manually or automatically injected into the air breathed by the patient through the breathing passage.

The method in accordance with the present invention of loosening phlegm and mucus plugs in a patient's airways and lungs basically comprises the steps of:

generating an acoustic waveform such as a sequence of sonic pulses in an acoustic signal generator;

directing the waveform directly into the patient's airways while the patient breathes in and out;

sensing a signal representative of the patient's respiration such as the sound of the patient's breathing;

feeding the representative signal back to the acoustic signal generator; and adjusting a portion of the waveform generated by the acoustic signal generator to the representative signal to thereby approximate at least a portion of the sound of the patient's breathing.

More generally, the method of the invention comprises the steps of:

sensing a parameter representative of a patient's breathing efficiency such as breathing sounds or blood oxygen levels;

generating an acoustic waveform in an acoustic generator;

directing the waveform into the patient's airways while the patient breathes in and out; and adjusting the generated acoustic waveform to optimize the effect on the sensed parameter.

In the case of sensing the sound of a patient's breathing, the step of adjusting preferably may include matching at least a portion of the frequency spectrum of the sensed sounds of the patient's breathing in the acoustic generator such that the generated waveform closely corresponds to the sensed frequencies.

The first embodiment of the present invention is entirely manually adjusted. To operate the apparatus of the first embodiment of the invention, the user inserts the mouthpiece of the apparatus into his or her mouth and breathes normally, inhaling and exhaling through the breathing passages. The user turns on the apparatus and the transducer produces an acoustic waveform which may be a continuous waveform or a series of sonic pulses which are directed through the sonic air coupling chamber into the user's lungs through the central aperture in the mouthpiece. The apparatus includes controls for the user to vary the continuous or intermittent mode of operation, the amplitude, repetition rate, frequency and the frequency mixture of the transmitted sound waveform so that the user can manually select the particular optimum combination for his or her condition.

Another, second embodiment of the apparatus in accordance with the present invention further includes an automatic mode of operation, which utilizes an acoustic feedback circuit to the acoustic generator transmitting the sound pulses or sound spectra that is designed to optimize one or more monitored parameters. The feedback circuit includes a sensor for detecting and monitoring a parameter such as the pitch or frequency spectrum of sounds produced by the patient when exhaling and inhaling between active pulse emissions, when operating in the pulse mode. Blood oxygen level is another exemplary monitored parameter which is particularly suited for use when the apparatus is operated in the continuous waveform generating mode.

The feedback circuit preferably automatically compensates or adjusts the waveform, e.g., amplitude, frequency, frequency spectrum and/or repetition rate produced by the acoustic generator of the apparatus to optimize the effect on the parameter being monitored. This second embodiment may be switched by the user between manual and automatic modes of operation. This embodiment preferably utilizes an analog to digital converter (ADC) coupled to a microprocessor or digital signal processor (DSP) to provide the feedback signal from the user's monitored parameter to automatically adjust the generated waveform in order to optimize the monitored parameter.

One example involves monitoring the sound of the user's breathing. In this case, the transducer itself may be used, in between the pulses in pulse mode, as a listening sensor (microphone) to pick up and amplify the user's breathing sounds between periods of operation. When a digital signal processor is used, the transducer itself may be used even during waveform transmission, to listen to the user's breathing sounds by canceling out the transmitted waveform using digital sampling techniques. Alternatively, a separate microphone may be provided. The optimum result is provided, in the case of monitoring the sound of the patient's breathing, when the frequency spectrum produced by the apparatus substantially matches the spectrum of the user's breathing or wheezing sounds.

In the case where blood oxygen level is monitored, the optimum is provided when the monitored oxygen level is maximized. In this case, the DSP may include generation of a predetermined or preprogrammed sequence of frequency spectrums to be generated and tested to systematically determine where the maximum benefit on oxygen level is obtained.

Another example of a monitored parameter may be an ultrasonic monitor which senses an ultrasonic signature of a mucus plug. When a person has mucus plugs that restrict air passage, often an ultrasonic signature is produced by the patient's breathing around this plug. The presence of this ultrasonic signature can be used to trigger generation of an acoustic waveform search pattern. As the frequency of the acoustic waveform generated pattern approaches and then matches the resonance frequency of the mucus plug, the ultrasonic signature of the plug will change. This change is detected and signals to the acoustic generator that the resonant frequency, i.e. optimal frequency for mucus plug loosening, has been reached. The acoustic generator then reproduces the resonant frequency waveform to further loosen the mucus plug The apparatus in accordance with the present invention may be operated for as long as needed by the user. The user need only remove the mouthpiece while coughing to expel phlegm and mucus loosened by the vibrations of the generated waveform or sound pulses transmitted directly into the user's lungs.

Another unique feature of the present invention is that it is sound damped, i.e., virtually all of the sound produced by the acoustic transducer is directed through the air chamber into the user's bronchial tubes and lungs and not out through the walls of the apparatus. Therefore a user may utilize the apparatus in a crowded environment without disturbing others in the immediate vicinity. The cavity behind the acoustic transducer is filled with an absorptive material which dissipates resonances in the cavity behind the transducer and absorbs energy from the rear of the transducer to improve forward transmission efficiency.

The apparatus of the invention may be either battery powered by conventional batteries or may be powered from normal house current. The power supply in the apparatus may also include rechargeable batteries for use while traveling. Another embodiment of the present invention includes an elongated mouthpiece so that a nebulizer or aerosol dispenser may be attached to the mouthpiece to dispense medications into the user's airways during operation of the apparatus of the present invention. A further embodiment of the present invention may be separated into a power supply/electronics module and a transducer/mouthpiece module particularly adapted for neonatal care applications and critical care applications. These and other features and advantages will become more apparent from a reading of the following detailed description when taken in conjunction with the drawing figures.

BRIEF DESCRIPTION OF THE DRAWING

FIG. 2 is a sectional view of the apparatus in accordance with the present invention shown in FIG. 1.

FIG. 3A is an end view of the mouthpiece of the apparatus in accordance with the invention shown in FIG. 1.

FIG. 3B is an end view of an alternative mouthpiece of the apparatus shown in FIG. 1.

DETAILED DESCRIPTION OF THE INVENTION

Figure 1:
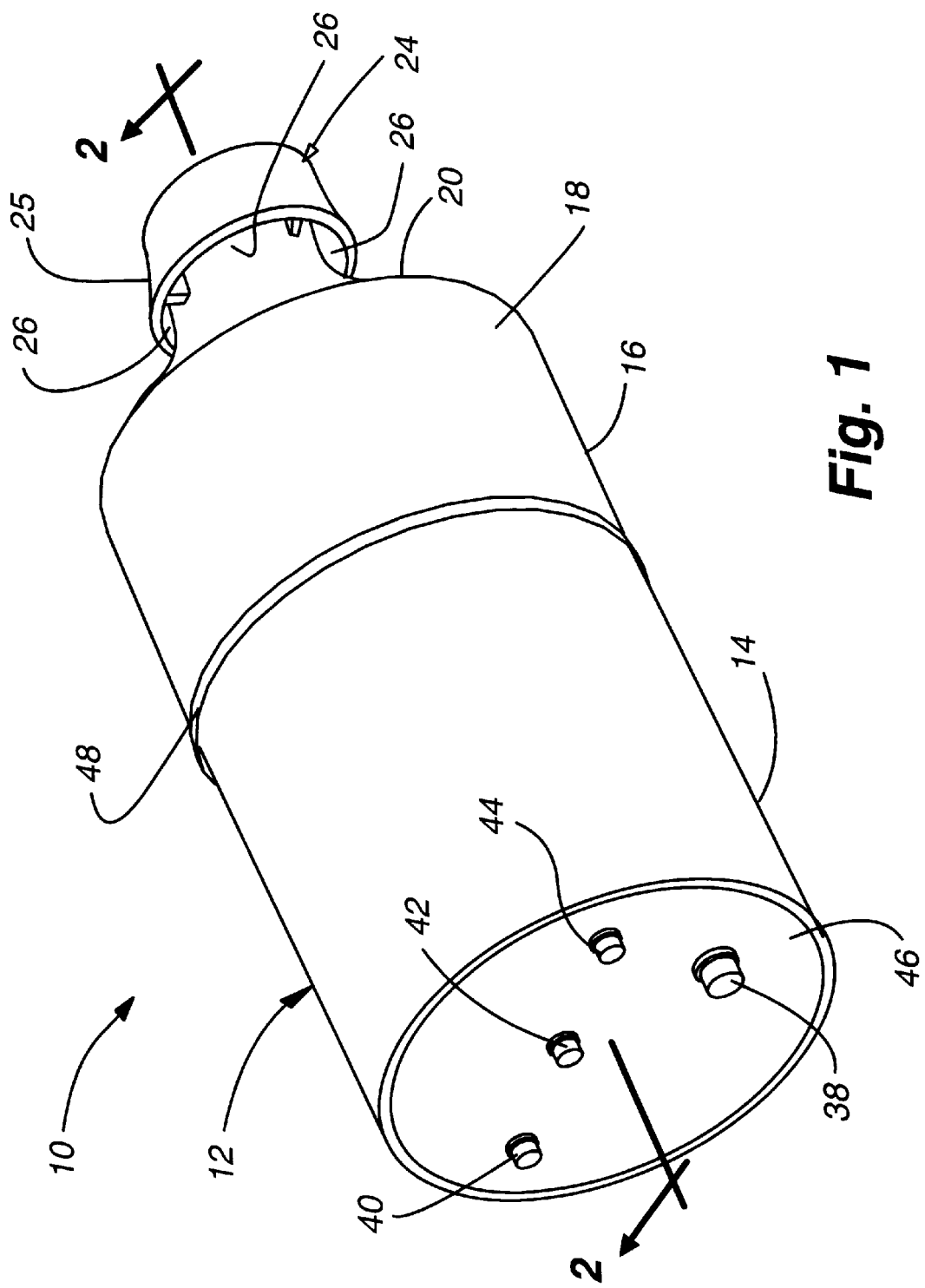
FIG. 1 is a perspective view of a first embodiment of the apparatus in accordance with the present invention.

Referring to FIG. 1, a first embodiment of an apparatus 10 in accordance with the present invention is shown in a perspective view. The apparatus 10 comprises a generally cylindrical housing 12 that has a bottom or base tubular portion 14 and a generally tubular cap portion 16. The cap portion 16 has a tubular side wall 18 and preferably a generally funnel shaped end wall 20 having a central aperture 22 therethrough connected to a preferably semi-rigid mouthpiece 24 designed to be held in the user's mouth between the teeth. The mouthpiece 24 preferably includes a peripheral sleeve 25 forming a plurality of breathing passages 26 extending alongside the body of the mouthpiece 24. An end view of the mouthpiece 24 is shown in FIG. 3A.

The peripheral sleeve 25 is spaced from the body of the mouthpiece 24 by axially extending ribs 50. These ribs 50 divide the annulus formed between the body of the mouthpiece 24 and the peripheral sleeve 25 into the plurality of tubular passages 26 which extend alongside the body of the mouthpiece 24 a sufficient distance, about an inch, so that the user does not cover their end openings with his or her lips. The breathing passages 26 allow the user to breath fresh air normally in and out through the mouth during operation of the apparatus 10. Although the passages are not required since the user can breathe through his or her nose, the passages are preferred since often a user may have constricted sinuses, a stuffy nose, etc. The width of the passages 26 shown in the FIGS. 1, 2, and 3A are shown exaggerated for clarity. In reality, the width is much narrower. The passages 26 have a total cross sectional area that is small compared to the area of the central aperture 22 through the mouthpiece 24 so that the sound transmitted through the central aperture 22 into the user's airways is not diverted out through the breathing passages 26.

An alternative arrangement of the tubular passages 26 in the mouthpiece 24' is shown in FIG. 3B. In this embodiment, the breathing passages 26' are comprised of actual short tubes 29 extending axially alongside the body of the mouthpiece 24. These tubes 29 are banded together around the body of the mouthpiece 24 and may be removed and replaced as may be required for cleaning.

The bottom or base portion 14 of the apparatus 10 contains an acoustic generator which comprises a battery power supply 28, a circuit board 30 containing an audio oscillator circuit 32 and an audio amplifier circuit 34 thereon, and supports an acoustic transducer 36 connected to the output of the audio amplifier 34. The transducer 36 is essentially a conventional speaker. As more fully described with reference to the second embodiment below, the transducer 36 may be a combination speaker/microphone which operates as a conventional speaker when electrically driven and as a microphone when acoustically driven by the patient's breathing sounds. An on/off/mode switch 38, volume control 40, frequency control 42, and a repetition rate control 44 are preferably accessible through apertures in a disk shaped bottom plate 46 closing the bottom or base of the tubular portion 14.

These four switches shown are exemplary and may be replaced by a different combination of switches with the functions designated by button sequences or combinations. For example, there may be only three buttons or switches 38, 40 and 42. In this case button 38 alone could turn the apparatus on or off and pressing switch 38 twice in succession could switch between pulse and continuous modes. Both switches 38 and 40 depressed together could increase the volume. Switch 40 alone could decrease the volume. Both switches 38 and 42 depressed together could increase the frequency and depressing switch 42 alone could decrease the frequency. Switches 40 and 42 depressed simultaneously could change repetition rate. Two switches may also be used. In this case, pressing both together once could turn the unit on. Pressing both together twice could switch between continuous and pulse modes. Pressing both together and holding for a predetermined period of time could turn the apparatus off. Pressing and holding one of the switches would increase the volume. Pressing and holding the other switch would increase the frequency. Pressing and holding the first switch again could decrease the volume, pressing both simultaneously could change to the repetition rate adjust mode and so on. Other combinations readily apparent to those skilled of the art may also be utilized and may easily be facilitated. The configuration shown is merely an illustrative example.

The base tubular portion 14 and the cap portion 16 are preferably telescopically mated together with a replaceable elastic diaphragm 48 captured therebetween, i.e., captured by the telescoping ends of the tubular portions 14 and 16. The purpose of the diaphragm 48 is primarily to prevent biological contaminants from reaching the transducer cone 37 and the electrical components in the lower portion 14 of the housing 12. Accordingly, the diaphragm 48 may be either reusable or disposable. Alternatively, the cap portion 16 and diaphragm 48 may be integrally made as a single disposable unit.

It is contemplated, however, that the diaphragm 48 may not always be a necessary or integral component of the acoustic transceiver apparatus 10. Under circumstances where the entire apparatus is disposable or where the apparatus can be sterilized between uses it may be preferable to produce and use the apparatus without a diaphragm barrier.

The cap portion 16, the diaphragm 48 over the cone 37 of the transducer 36, and the mouthpiece 24 together define an acoustic coupling chamber 27 which couples the transducer 36 to the user's airways when the mouthpiece 24 is held in a user's mouth. When the diaphragm 48 is provided as a separate piece, the diaphragm 48 is preferably stretched over the bottom end of the cap portion 16 during housing assembly and then the cap portion 16 is slipped over the open transducer end of the bottom portion 14. In this way, when the apparatus 10 is disassembled for cleaning after use, the cap portion 16, diaphragm 48, and mouthpiece 24 can be removed as an assembly. The component parts may then be cleaned and/or sterilized and the diaphragm 48 replaced as may be necessary.

Alternatively, the diaphragm 48 may be first installed over the cone 37 of the transducer 36 on the bottom portion 14 and/or the cap portion 16 may alternatively be sized to fit within the open end of the bottom portion 14. The cap portion 16 and base portion 14 may also be constructed to be mated in any other conventional manner.

The diaphragm 48 may optionally be an annular disk of thin elastic material with a relatively rigid rim which fits snugly within either the cap portion 16 or within the bottom portion 14. The diaphragm 48 may also be designed to slip over one of the portions 14 or 16 with a semi rigid rim snap fitting within an external groove or internal groove in one of the portions (not shown). In any event, the diaphragm 48 is placed so as to shield the transducer cone 37 from any contaminants that may be exhaled by the user of the apparatus 10 of the invention but still transmit sound vibrations therethrough from the transducer 36 into the acoustic chamber 27 of the cap portion 16 and into the user's airways.

The mouthpiece 24 may be a separate piece physically attached to the exterior of the cap portion 16. In this case, the ribs 50 may frictionally grip or be adhesively bonded to the end wall 20 around the aperture 22. Alternatively, the cap portion 16 and the mouthpiece 24 may be formed as a one piece molded structure. In this instance, the inside surface of the cap portion 16 and mouthpiece 24, together with the cone of the transducer 37, define the coupling chamber 27. The mouthpiece 24 as shown in FIGS. 1, 2, and 3A may be either separately formed or may be integrally molded into the cap portion 16.

Since the diaphragm 48 is elastic, supple and flexible, its presence is virtually transparent to the sound transmission from the transducer 36 through the sonic coupling chamber 27 into the patient's airways during use. The transducer 36 is preferably sized so that the outer diameter of the cone 37 is approximately the same as the internal diameter of the tubular bottom portion 14. The transducer 36 nests in the tubular bottom portion 14 and the cone faces the cap portion 16 and the diaphragm 48. The transducer preferably is of a compact, high efficiency design so as to minimize power drain.

The space behind and around the rear of the transducer cone 37 in the base portion 14 of the housing 12 is preferably filled with a sound absorptive material 39. This sound dampening material 39 may be a fibrous batting such as cotton, etc. The purpose of this material 39 is to prevent substantive sound transmission outside of the base portion 14 of the housing 12 except forward through the sonic coupling chamber 27 and through the aperture 22 in the mouthpiece 24 into the patient's airways and lungs. Thus the material 39 dissipates resonances in the cavity behind the transducer cone and absorbs energy from the rear to increase forward sound transmission efficiency. However, the presence of this absorptive damping material has an adverse affect on power consumption. The amplifier output must be increased in order to overcome the drag on the cone 37. It is believed that the power output of the transducer 36 during operation as a speaker should thus preferably be within a range of around 5 to 7 watts in order to maintain efficiency and effectiveness of pulse delivery, although other power requirements may be specified in specific applications.

A patient breaths fresh air through the passages 26 around the aperture 22 while holding the mouthpiece 24 in his or her mouth. The continuous acoustic waveform or sound pulses emitted by the transducer 36 are focused through the aperture 22 directly into the patient's airways. Simultaneously, the patient breathes normally through the passages 26 which open to the air external to the chamber 27. Sound is substantially prevented from escaping the housing 12 when the continuous acoustic waveform or sonic pulses are being produced primarily because of the size of the passages 26 and the presence of the damping material 39 behind the transducer 36. Each of the mouthpiece passages 26 has an effective diameter that is much smaller than the predominant wavelengths of the sounds being generated by the transducer 36, on the order of less than 0.5 inch. For example, the wavelength of a 60 hertz sound is 18 feet. The wavelength of a 1000 hertz sound is 1.09 feet, and 10,000 hertz is 0.1 foot. The effective passage diameter for each passage is preferably on the order of 0.050 inches to 0.075 inches, or 0.004 feet, which is preferably at least an order of magnitude smaller than the wavelength of the sound being transmitted. The most effective frequencies of interest are believed to be less than 10,000 hertz. The apparatus 10 in accordance with the invention may, however, have any frequency range. A range between 10 hertz and 10,000 hertz is presently preferred.

Users will most likely utilize frequencies between 20 to 4000 hertz, as these are the frequencies most often associated with phlegm vibration. For most frequencies of interest, the effective diameter of the breathing passages 26 is thus at least one to two orders of magnitude smaller than the wavelengths of the sounds produced. Since these passages 26 are substantially smaller than the wavelengths of interest, little sound pressure will be lost from the chamber 27 even when their combined effect is considered. However, these passages are important because they permit the user to breath substantially normally while using the apparatus 10.

The passages 26 may be located anywhere in or around the walls of the sonic coupling chamber 27. For example, they may alternatively be located in the side wall 18, the end wall 20, or around the mouthpiece 24. The mouthpiece 24 shown in FIGS. 1, 2, and 3A is preferred in the present invention. The size of the passages 26 may also be larger than described above, if other means of preventing substantial loss of acoustic pressure waves is provided. For example, the passages 26 may be partially covered by an integral baffle arrangement molded or otherwise formed within the mouthpiece 24 or the cap portion 16. Other sonic guide and focusing structures may also be provided within cap portion 16 to enhance the sonic pressure pulse transmission into the user's airways and lungs.

As stated above, the space behind the transducer cone 37 is substantially filled with sound damping material 39. The presence of this absorptive material and the lack of holes in the tubular wall of the base portion 14 to equalize pressure requires that net power delivered to the transducer 36 must be increased due to the drag this closed space provides on the transducer cone 37. However, this drag is small compared to the advantage of preventing unwanted noise projection outside of the housing 12. In addition, the damping material 39 increases the forward sound transmission efficiency. Thus, in operation, a person sitting or standing next to the user will barely detect any sound from the apparatus 10 while it is being used.

The space between the diaphragm 48 and the transducer 36 is closed. However, because the diaphragm 48 is very flexible and resilient, made of preferably a very elastic material such as latex or synthetic rubber, little acoustic attenuation results and the sound pulses effectively are transmitted through the diaphragm unimpeded from the transducer 36 through the coupling chamber 27. The cylindrical wall 18 of the cap portion 16 may optionally be shortened such that it is almost flush with the diaphragm 48. The shape of the end wall 20 may also be other than the funnel shape as shown.

Figure 4:
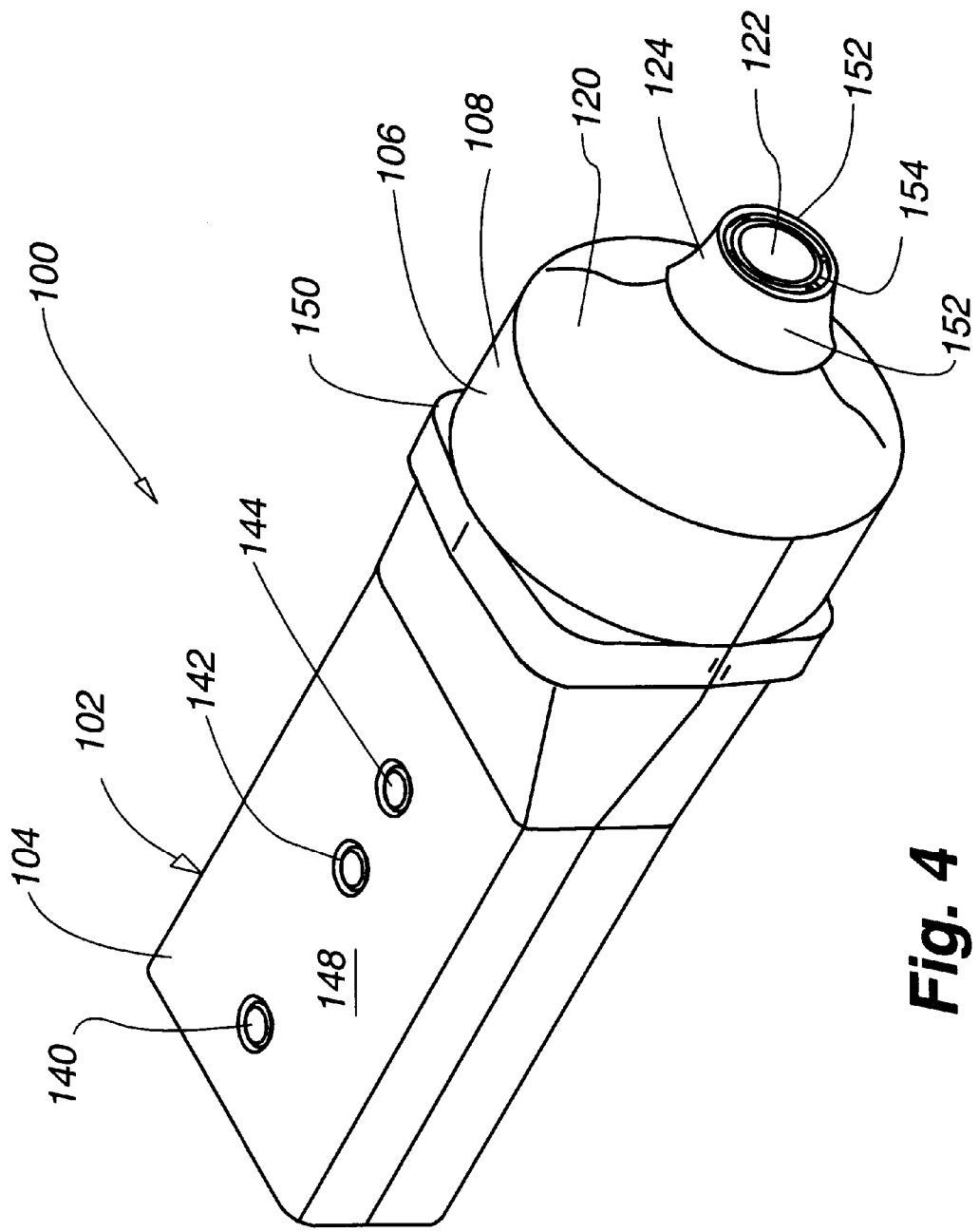
FIG. 4 is a perspective view of a second embodiment of the apparatus in accordance with the present invention.
Figure 5:
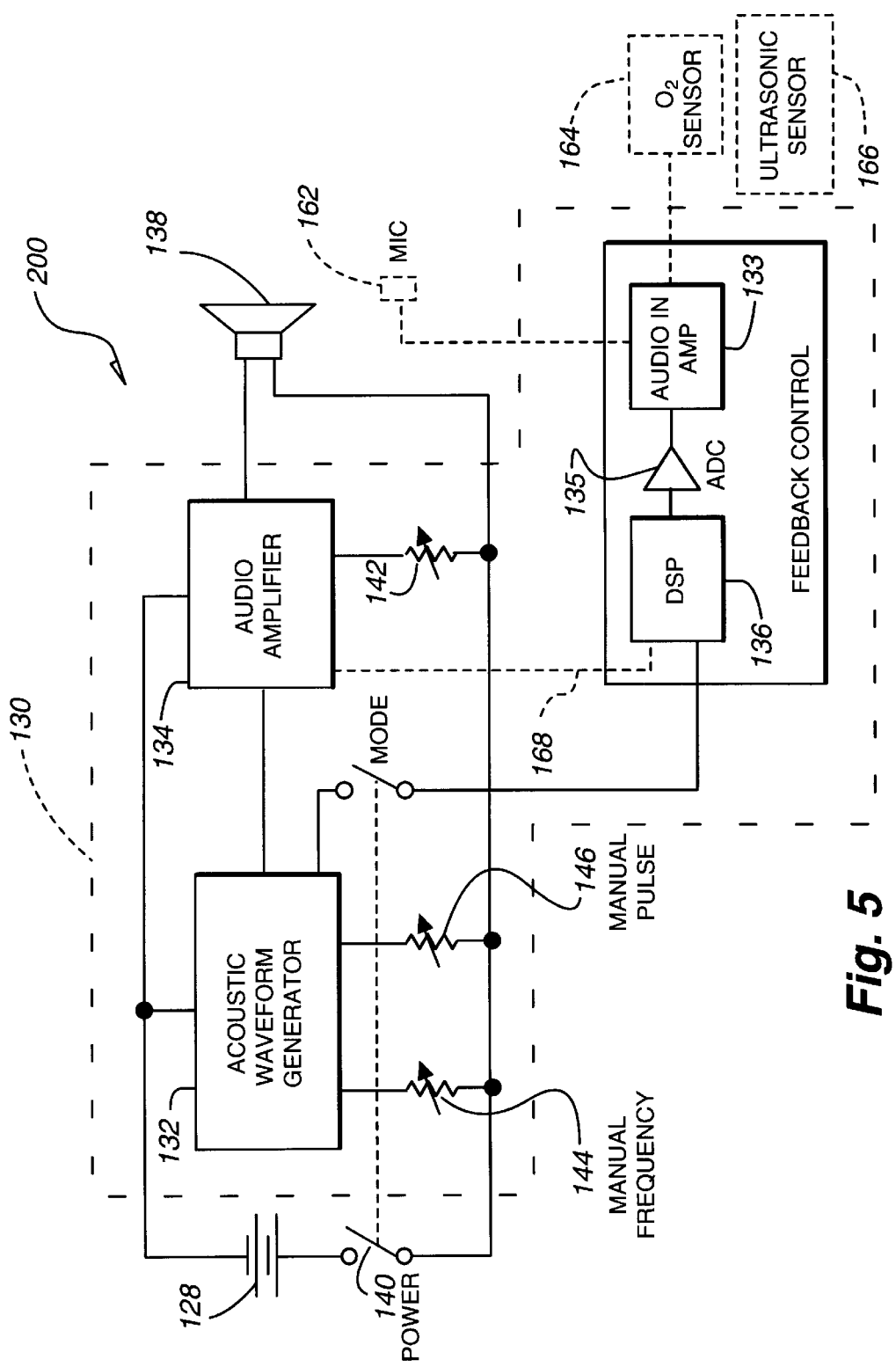
FIG. 5 is a schematic block diagram of the electrical circuit of the apparatus shown in FIG. 4.

A second embodiment 100 of the present invention is shown in FIGS. 4 and 5. This embodiment illustrates one alternative shape variant. The apparatus 100 comprises a hollow housing 102 that has a bottom or base portion 104 and a cap portion 106. The cap portion 106 has a tubular side wall 108 and a funnel shaped end wall 120 having a central aperture 122 and a semi-rigid mouthpiece 124 formed around the aperture 122 designed to be held in the user's mouth between the teeth.

The bottom or base portion 104 has a generally rectangular box portion containing a battery power supply 128 and an acoustic generator comprising a circuit board 130 containing an audio oscillator circuit 132, an audio in amplifier circuit 133, an audio amplifier circuit 134, an analog to digital converter 135, and a digital signal processor 136. (See FIG. 5) The audio amplifiers 133 and 134 are connected to an audio transducer 138. An on/off/mode switch 140, volume control 142, and frequency control 144 are accessible through apertures in the wall 148 of the base portion 104. A repetition rate control 146 is actuated by pressing switches 142 and 144 simultaneously. The audio oscillator/waveform generator circuit 132 generates an acoustic waveform which may be continuous or broken into sonic pulse signals which are in turn fed to the audio amplifier 134 and then to the transducer 138 which generates the actual sounds.

The mating ends of the base portion 104 and the tubular cap portion 106 are preferably telescopically joined together as in the first embodiment described above. A replaceable elastic diaphragm 150 is preferably captured between the telescoping ends of the tubular portions 104 and 106. The purpose of the diaphragm 150 is again to act as a biological shield primarily to prevent contaminants from reaching components in the lower tubular portion 104 of the housing 102. Accordingly, the diaphragm 150 may be reusable or disposable. Alternatively, the diaphragm 150 may be integrally formed with the cap portion 106 so as to be disposable as a unit. The cap portion 106, the cone of the transducer 139, and the mouthpiece 124 together define an acoustic coupling chamber 127 which couples the transducer 138 to the user's airways when the apparatus 100 is placed in a user's mouth.

In the embodiment shown in FIGS. 4 and 5, the diaphragm 150 is preferably stretched over the bottom end of the cap portion 106 and then the cap portion 106 is slipped over the open transducer end of the bottom portion 104. In this way, when the apparatus is disassembled after use, the cap portion 106, diaphragm 150, and mouthpiece 124 are removed as an assembly. The component parts may then be disassembled, cleaned or sterilized, or replaced as in the first embodiment discussed above.

Alternatively, the diaphragm 150 may be first installed on the bottom portion 104 and/or the cap portion 106 may alternatively be sized to fit within the open end of the bottom portion 104. The diaphragm 150 may optionally be an annular disk of thin elastic material with a relatively rigid rim which fits snugly within either the cap portion or the bottom portion 104. In any event, the diaphragm 150 is placed so as to shield the transducer cone 139 from any contaminants that may be exhaled by the user of the apparatus of the invention but still transmit sound vibrations therethrough into the cap portion 106.

Preferably the mouthpiece 124 is integrally formed with the cap portion 106 as a one piece molded structure. In this instance, the cap portion 106 and mouthpiece 124, together with the cone of the transducer 139, define the coupling chamber 127. Since the diaphragm 150 is elastic, supple and flexible, its presence is virtually transparent to the sound transmission from the transducer 136 through the sonic coupling chamber 127 into the patient's airways during use. The mouthpiece 124, the cap portion 106 and the diaphragm 150 may be manufactured as a disposable self contained unit rather than being separable into its component parts.

The transducer 138 is preferably sized so that the outer diameter of the vibrating cone 139 is approximately the same as the internal diameter of the tubular cap portion 106. The transducer 136 preferably nests in the rectangular box portion 104 and the cone faces the cap portion 106 and the diaphragm 150 as in the first embodiment. The transducer 138 preferably is of a compact, high efficiency design so as to minimize power drain. The power output of the transducer in this embodiment is generally similar to that of the first embodiment. Thus the effective power output should preferably be in the range of 5 to 7 watts for the same reasons. This power limitation may optionally be designed into the amplifier circuitry to preclude inadvertent over stimulation of sensitive lung tissues.

The bottom portion 104 differs from the first embodiment primarily in that it includes a closed rectangular part to house the power supply 128 and printed circuit board 130. This rectangular part of the bottom portion 104 may be a clam shell design that snaps closed. The front part 151 of the bottom portion 104 is shaped to closely enclose the transducer 138. The portion 104 behind the transducer cone is again filled with a sound absorbing material such as cotton batting or foam as in the first embodiment 10. This configuration eliminates or reduces substantially the sound transmitted outside the apparatus 100 during operation of the device. Consequently, power to the transducer or other acoustic transducer 138 must be increased as discussed above to compensate for the power lost in overcoming the damping effect of this closed and at least partially filled volume behind the transducer cone. The space between the diaphragm 150 and the front face of the transducer 138 is also a closed space. However, because the diaphragm 150 is very flexible and resilient, made of preferably a very elastic material such as latex, polypropylene, synthetic rubber, or other plastic fiber, little acoustic attenuation results and the sound pulses effectively are transmitted by the transducer cone through the diaphragm unimpeded from the transducer 138 through the coupling chamber 127. Again, one major advantage of this second embodiment is that the apparatus 100 is very quiet to operate and may be operated by a patient in close proximity to other people without substantially interfering with their activities.

The funnel shaped tubular side wall of the cap portion 106 is solid and smoothly curves into the mouthpiece 124. In order for the user to breathe through the sonic coupling chamber 127 while using the apparatus 100 in accordance with this embodiment of the present invention, one or more passages is formed by a segmented annular sleeve 152 supported by and integral with the mouthpiece 124. This sleeve 152 forms a plurality of coaxial passages 154 around the mouthpiece 124 as in the first embodiment which together form a large enough passage to the outside environment for the patient to breath through. Each of the passages 154 has a width of between $\frac{1}{16}$ to about $\frac{1}{8}$ inch. Each passage 154 width is much smaller than the wavelength of the sounds being generated by the transducer 138. Since the widths are substantially smaller than the acoustic wavelengths of interest, little sound pressure will be lost from the chamber 127 even when their combined effect is considered.

The bottom portion 104 differs from the first embodiment 10 in that not only does it have a closed volume behind the transducer 138, the transducer 138 preferably operates as a microphone between active pulses, i.e., between transmitted bursts of sound. The transducer 138 acts as a microphone to produce electrical signals representative of the patient's breathing sounds and feeds these signals to the amplifier circuit 200 shown in FIG. 5.

It has been found that when a patient's lungs are stimulated with a sound spectrum that substantially corresponds to the sound of the patient's wheezing, the phlegm causing the wheezing sound is specifically targeted and loosened. It appears that the wheeze sound may be substantially the resonant frequencies of the phlegm and mucus plugs. Consequently, if the resonant frequencies can be sensed and duplicated or targeted, dislodging the phlegm and mucus plugs almost immediately ensues. Therefore, this second embodiment 100 of the apparatus of the invention includes an automatic tone generation/adjustment feature.

In addition to having the manually variable pitch and duration controls as described above with reference to the first embodiment, this second embodiment 100 includes a feedback function which senses a parameter indicative of a user's breathing efficiency and uses the sensed parameter to automatically adjust the output acoustic waveform to optimize the device's affect on the monitored parameter. The monitored parameter, in the illustrated second embodiment, is preferably the sound produced by the user during breathing. This second embodiment 100 includes an audio in amplifier 133 connected to the transducer 138 which receives and amplifies sound signals received from the transducer 138, for example, in the pulse mode, when the transducer is between pulses, i.e. when the transducer 138 is "listening". The audio amplifier 133 is connected to the ADC 135 which is in turn connected to the DSP 136. The DSP 136 is connected through the off/on/mode switch 140 to the acoustic waveform generator 132.

Alternatively, the DSP 136 may be used to digitally directly generate the acoustic waveform. In this instance it may be connected directly to the audio amplifier 134 as shown by the dashed line 168 in FIG. 5. The DSP 136 may be utilized to detect the sound of a patient's breathing even during transmission of the acoustic waveform to the user via digital sampling techniques to cancel out the transmitted waveform, which unmasks the user's breathing sounds.

During or between pulses, and preferably whenever the apparatus 100 is on but not generating an acoustic waveform, the transducer 138 senses the patient's breathing sounds. The DSP 136 processes these sound signals and produces a feedback signal to the oscillator/pulse generator 132 to produce an output sonic waveform that closely matches in frequencies the respiration sound from the patient. This automatic frequency adjustment or matching may be turned on and off by the user/patient preferably via operation of the switch 140.

The apparatus 100 may alternatively utilize a separate microphone 162, as shown dotted in FIG. 5, rather than the transducer 138. In addition, the embodiment 100 may include detection of separate parameters which may have a bearing on the success of the therapeutic apparatus of the present invention. For example, the input amplifier 133 or the signal processor 136 may be connected to an external parameter sensor such as a blood oxygen sensor 164 or an ultrasonic sensor 166. In the former instance, the volume, pitch and/or frequency spectrum output of the transducer 138 may be optimized to achieve maximum blood oxygen levels. In this case, the frequency and pulse duration produced by the apparatus 100 would be varied by the signal processor 136 in a predetermined pattern or sequence until the optimum level of oxygen is sensed.

Similarly, if an ultrasonic sensor is utilized, the sensor 166 may be utilized to first identify any signatures of mucus plugs present in the user's lungs via "listening" to the user's breathing sounds; second, initiating generation of a predetermined "hunting" sequence of acoustic waveforms and then third, monitoring the mucus plug signatures to detect a change in the signature during the hunting sequence. Such a change in mucus plug signature is believed to occur when the generated waveform closely matches to the resonant frequency or frequencies of the mucus plug. Finally, the sensed change in ultrasound signature is used to cause the acoustic generator to stop the predetermined sequence and reproduce the waveform that caused the signature change until the plug is loosened and the user coughs up the mucus plug. This hunting process may then be repeated until no further ultrasonic signatures or signature changes are detected.

The major advantage of this second embodiment is that it can automatically "zero in" on the resonant frequencies of the obstructions to efficient breathing and thereby optimize efficient loosening of mucus plugs and phlegm. Further, the apparatus 100 is very quiet to operate and may be operated without the patient consciously monitoring and manipulating its operation. In addition, it may be operated by the patient in close proximity to other people without substantially interfering with their activities.

Figure 6:
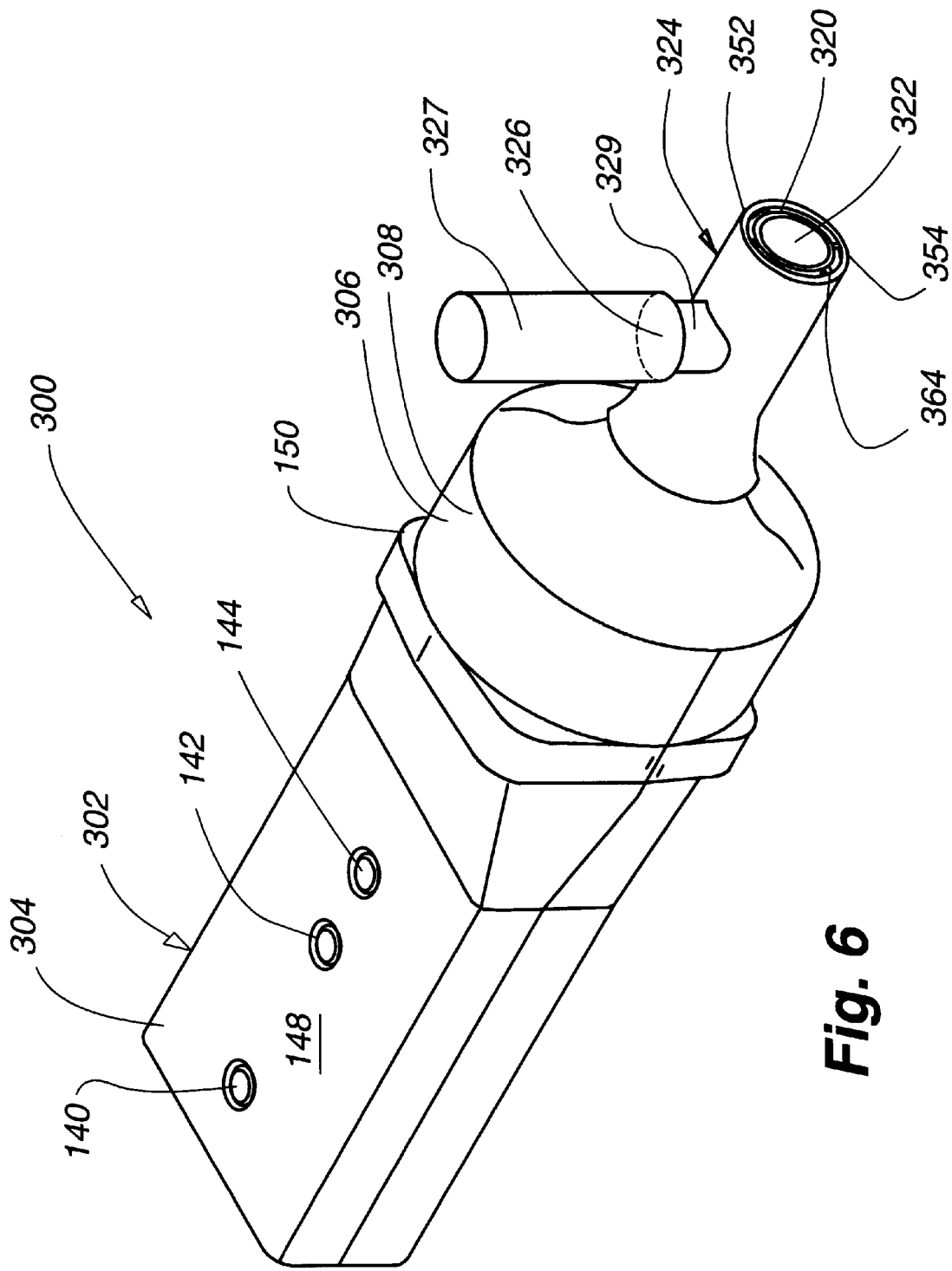
FIG. 6 is a perspective view of a third embodiment of the present invention.

A third embodiment of the present invention is shown in perspective view in FIG. 6. This embodiment is similar to the second embodiment described above with an elongated mouthpiece adapted to receive an aerosol dispenser. The apparatus 300 comprises a hollow housing 302 that has a bottom or base portion 304 and a cap portion 306. The cap portion 306 has a tubular side wall 308 and a funnel shaped end wall 320 having a central aperture 322 and an elongated, semi-rigid mouthpiece 324 formed around the aperture 322 designed to be held in the user's mouth between the teeth.

The bottom or base portion 304 has a generally rectangular box portion, as shown in FIG. 4 and FIG. 5, containing the battery power supply 128 and the acoustic generator comprising a circuit board 130 containing an audio oscillator circuit 132, an audio in amplifier circuit 133, an audio amplifier circuit 134, an analog to digital converter 135, and a digital signal processor 136. The audio amplifiers 133 and 134 are connected to an audio transducer 138. An on/off/mode switch 140, volume control 142, and frequency control 144 are accessible through apertures in the wall 148 of the base portion 104. A repetition rate control 146 is actuated by pressing switches 142 and 144 simultaneously. The audio oscillator/waveform generator circuit 132 generates an acoustic waveform which may be continuous or broken into sonic pulse signals which are in turn fed to the audio amplifier 134 and then to the transducer 138 which generates the actual sounds.

The mating ends of the base portion 304 and the tubular cap portion 306 are preferably telescopically joined together as in the second embodiment described above. A replaceable elastic diaphragm 150 is preferably captured between the telescoping ends of the tubular portions 304 and 306. The purpose of the diaphragm 150 is again to act as a biological shield primarily to prevent contaminants from reaching components in the lower tubular portion 304 of the housing 302. Accordingly, the diaphragm 150 may be reusable or disposable. Alternatively, the diaphragm 150 may be integrally formed with the cap portion 306 so as to be disposable as a unit.

The funnel shaped tubular side wall 308 of the cap portion 306 is solid and smoothly curves into the mouthpiece 324. The mouthpiece 324 is comprised of a tubular end of the funnel shaped end wall 320 defining the central aperture 322 and a generally tubular sleeve 352 which is spaced from the end wall by a plurality of ribs 364. The ribs support a series of breathing passages 354 that extend the length of the mouthpiece 324.

In order for the user to breathe through the sonic coupling chamber 127 while using the apparatus 300 in accordance with this embodiment of the present invention, one or more passages is formed by a tubular sleeve 352 supported by and integral with the mouthpiece 324. This sleeve 352 forms a plurality of coaxial passages 354 around the mouthpiece 324 as in the first embodiment which together form a large enough passage to the outside environment for the patient to breath through. The length of the mouthpiece 324 has been extended to permit a port 326 that complementary receives an aerosol spray medicine dispenser 327 therein. This permits the user to attach a dispenser to the mouthpiece 324 and dispense medications into his or her lungs while using the apparatus 300.

In more detail, as shown in FIG. 6, the port structure 329 extends away from the topside of the mouthpiece 324. The port structure is defined by the outward extension of the tubular sleeve 352 away from the tubular shaped end wall 320. The extension of the sleeve defines an open ended shaft shaped such that it will receive a pharmacological agent dispensing device 327. A plurality of ribs 364 support the tubular sleeve 352 and port structure 329 on the end wall 320. In this embodiment it is envisioned that the ribs be discontinuous along the length of the sleeve to allow the breathing passages and port to be in communication. It is also envisioned that the cavity defined by the port structure be large enough to accommodate the dispensed medication. The extension of the breathing passages away from the port structure are the same dimension as those described in the preceding embodiments.

An O-ring or other friction fitting material may be positioned against the interior surface of the port structure wall. The O-ring or other friction fitting material can be used to form a seal between the dispensing device 327 and the port structure to keep the atomized medication from escaping to the outside environment through the port aperture.

Note that it is contemplated that any structure, not simply the port structure, which allows for the application of the medication into the mouthpiece, could be utilized for the purpose described above in this third embodiment.

To use the third embodiment of the apparatus, the user simply compresses the dispensing device 327 during inhalation thus allowing the atomized medication to be dispensed into the port and breathing passages. As the user inhales, the medication is drawn along with the fresh air, through the breathing passages, and into the user's lungs. In this manner the user may apply medication while continuing the acoustic transceiver respiratory therapy.

When not in use the port can be sealed to the outside air by a plug, cap, valve or other suitable device.

Another alternative mouthpiece arrangement for dispensing medication is shown in FIG. 7. Here, the mouthpiece 324 includes an opening through the tubular sleeve 352 into breathing passages 354 to permit attachment of a nebulizer 355, either air or ultrasonic, or attachment of any other pharmaceutical dispensing device that dispenses aerosolized medication or gases through the passages into the user's airways and lungs.

In this alternative mouthpiece the aperture is defined by a port structure 329' that extends from the bottom side of the mouthpiece 324'. As described above the port is formed by the extension of the sleeve 352 away from the tubular shaped end wall 320. It is envisioned that the port structure 329' could have a valve 370 that responds to positive and negative pressure changes caused by the user's breathing. As such the port valve 370 would slide open under negative pressure allowing the medical spray to be inhaled into the user's lungs. Under the positive pressure of the user's exhalation the valve would slide shuts to seal the spray in the closed confines of the nebulizer 355.

This alternative mouthpiece 324' allows for the constant flow of medication to the lungs while using the apparatus.

An alternative way of attaching the nebulizer 355 to the port structure 329' is with vacuum tubing. The interaction between the port and tubing could be accomplished by means of a leur lock structure. As described above the port structure could have a pressure sensitive valve for release of the medication into the breathing passages. Note also that the use of vacuum tubing could facilitate the connection of a positive expiatory pressure device to assist the user in breathing and utilizing the phlegm breakup features of the present invention.

As an alternative to the breathing passages discussed in the third embodiment the breathing tubes 29 in the mouthpiece configuration shown in FIG. 3B may be used.

The embodiments 10, 100 and 300 may be constructed otherwise than as specifically disclosed above and shown with a reference to examples of preferred embodiments of the invention. Many changes, alterations and modifications may be made without departing from the scope of the invention. For example, the apparatus 10 is shown in a generally cylindrical housing. Other shapes may be utilized as well such as the combination shown in FIG. 4. The housing may also be telescopically expandable to provide an optimum coupling volume in a particular application or the housing may have an oval cross section or other cross sectional shape. A telescopically adjustable cap portion 16 with respect to base portion 14 would permit the sonic coupling chamber 27 to be tuned to various resonant frequencies in order to achieve optimum sonic pressure pulse delivery to the patient. The mouthpiece 24, end wall 22 and side wall 18 may be molded as an integral single unit. The bottom portion 14 may be much more compactly arranged and all components may be packaged with a rechargeable power supply rather than a battery pack or line cord. Also, the base portion 14 may include an integral pistol grip or other ergonomically desirable shape for the user to grasp during use.

Figure 7:
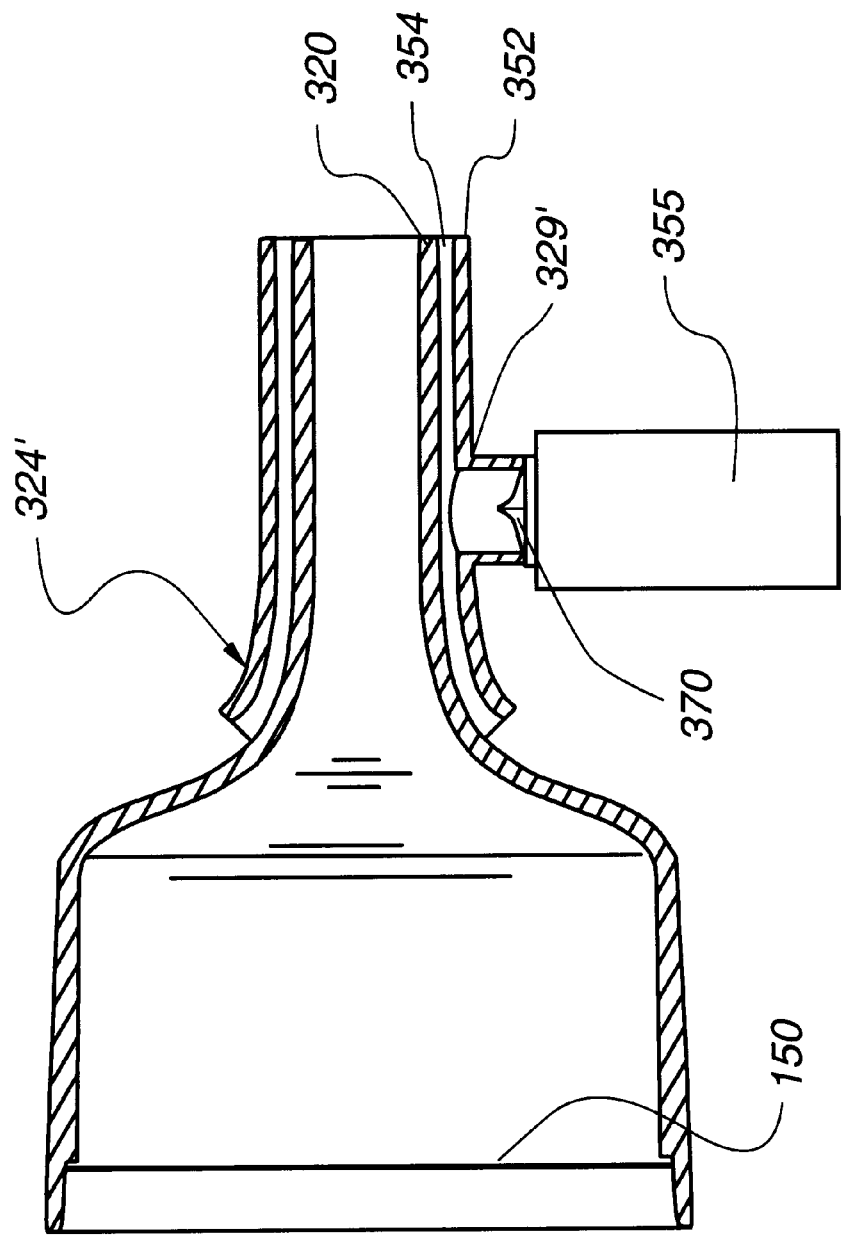
FIG. 7 is a cross sectional view of an alternative mouthpiece to the third embodiment shown in FIG. 6
Figure 8:
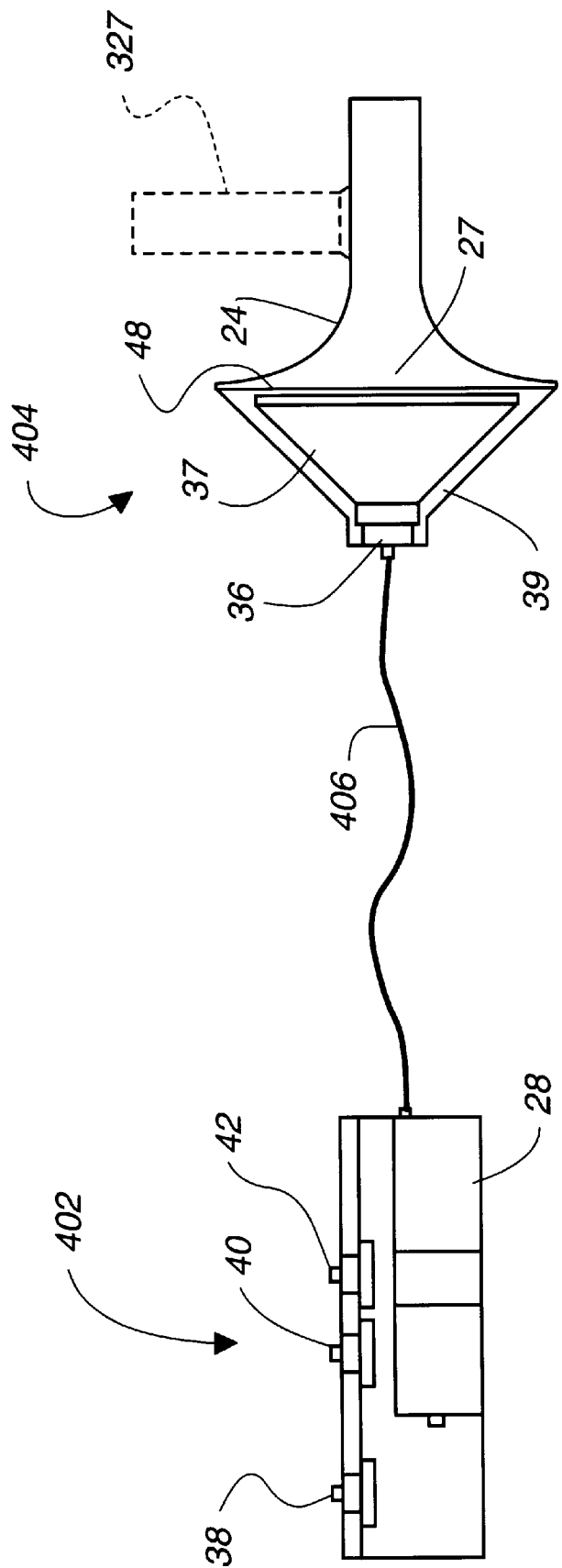
FIG. 8 is a fourth embodiment of the present invention modularized into a power supply module and a mouthpiece module.

Referring now to FIG. 8, the apparatuses 10, 100, and 300 may each be configured into two separate modules, a power supply module 402 and a transducer/mouthpiece module 404. The power supply module 402 would house the power supply, e.g. batteries, and the electronics controls and amplifier circuitry. The transducer/mouthpiece module 404 would contain the transducer 36 or 138, the diaphragm 48,or 150, and the mouthpiece 24, 124, or 324. The two modules 402 and 404 would be interconnected by wires 406 connecting the transducer 36 or 138 with the electronics 130 shown in FIG. 5. A medicinal dispenser 327 or nebulizer (shown in dashed lines in FIG. 8) may also be provided for and connected to the mouthpiece module 404 as in the embodiment shown in FIGS. 6 and 7.

Figure 9:
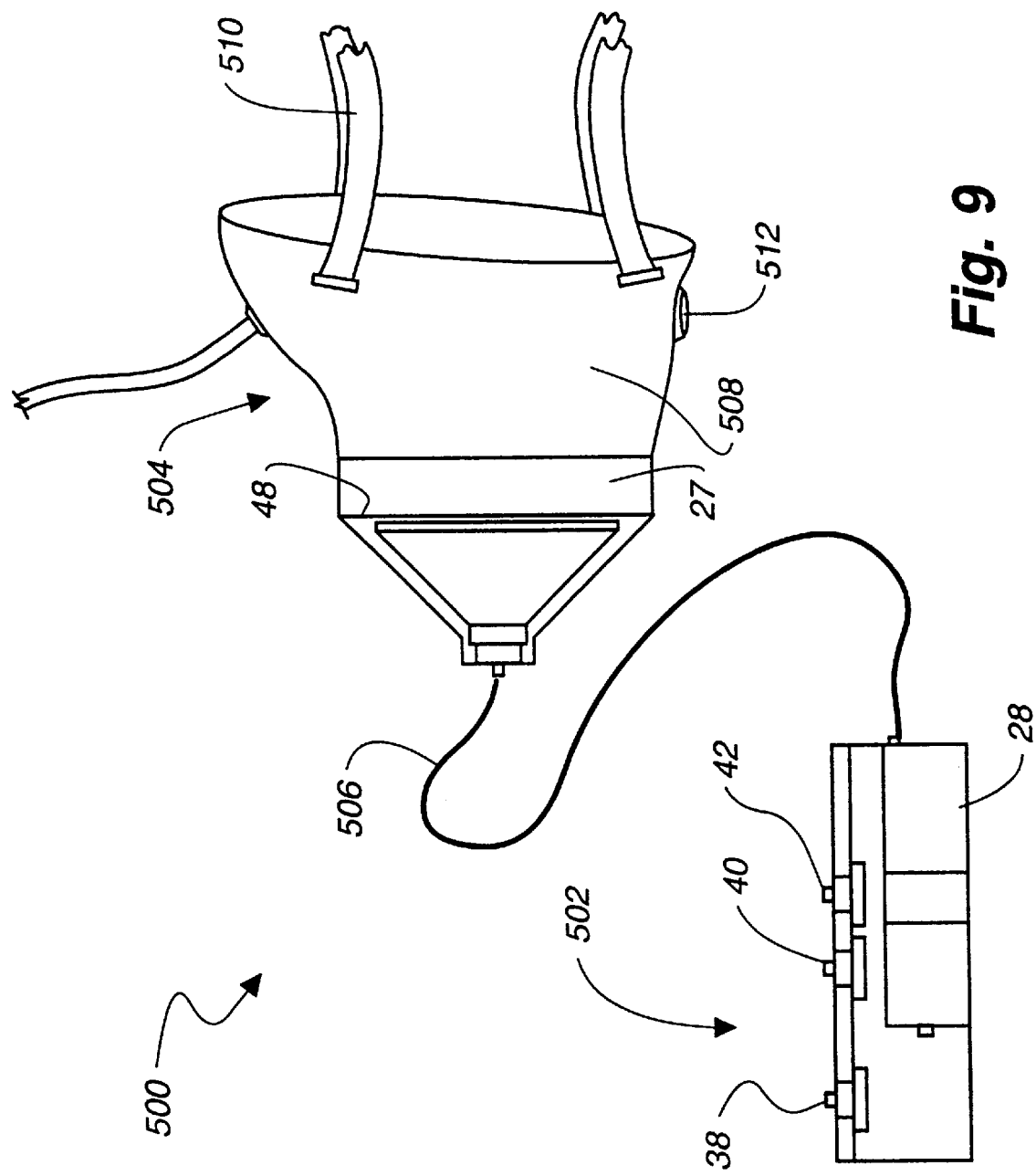
FIG. 9 is a fifth embodiment of the present invention modularized into a power supply module and a face mask module.

Finally, as an alternative to the transducer/mouthpiece module discussed in FIG. 8 the transducer may be integrated into a face mask as shown in FIG. 9. This embodiment has a transducer face mask module 504 in which the transducer 36 or 138 may be integrally formed with a cup shaped face mask portion 508. The face mask portion 508 is attached directly over a user's nose and mouth. The transducer/face mask module 504 could also contain the diaphragm 48 or 150 if the face mask module is designed to be reusable. If the module 504 is disposable the diaphragm may be omitted. As discussed above the power supply module 502 would house the power supply components, electronic controls and amplifier circuitry. Also as above, the two modules would be interconnected by wires 506 connecting the transducer 36, or 138, with the electronics shown in FIG. 5.

A plurality of elastic and/or hook and loop fastener straps 510 can be used to secure the mask portion 508 to the user's face. Other means may also be used for securing the mask to the face such as adhesive strips, although adjustable straps are preferred. The gases and medication are fed to the mask as in any standard type of medical use face mask.

It is also envisioned that the face mask could potentially accommodate a port structure 512 which extends away from the bottomside of the mask portion 508. The port structure would define an aperture from which any expelled mucus or phlegm may be either manually removed or removed using vacuum suction. When not in use the port could be sealed to the outside air by a plug, cap, valve or other suitable device.

The modular configuration shown in FIGS. 8 and 9 may be particularly suitable for applications in critical and neonatal care where the user may be incapable of handling and controlling the operation of the apparatus. Additionally, the mask configuration is also well suited for situations where the user is unable to hold or control the apparatus in the mouth.

The acoustic generator apparatus may also be configured to automatically trigger medication delivery or signal the need to manually dispense pharmacological agents based upon programmed levels of sensed parameters such as blood oxygen levels etc.

Accordingly, the invention is intended to encompass all such variations as will be readily apparent to those skilled in the art and is not limited to the embodiments shown and described above.

What is claimed is:

1. An apparatus for assisting a patient in loosening phlegm and mucus collected in a patient's lungs, bronchial and/or tracheal passages comprising:

a hollow housing having a cap portion and a base portion, said cap portion forming at least part of an acoustic coupling chamber, said cap portion including a mouthpiece around a portion of said chamber having at least one breathing passage therethrough leading out of said cap portion;

an audio signal generator having an acoustic transducer coupled to said chamber, said generator transmitting an acoustic waveform into said coupling chamber;

said mouthpiece coupling the acoustic coupling chamber into a patient's airways when the mouthpiece is held in a patient's mouth and permitting a patient to breathe through the breathing passage while said coupling chamber directs said acoustic waveform from said acoustic transducer into a patient's airways; and connection means on said mouthpiece for connecting a pharmaceutical dispensing device into said breathing passage so that a pharmaceutical material may be dispensed into such a patient's airways while such a patient breathes through said breathing passage.

2. The apparatus according to claim 1 wherein the cap portion is removable from the base portion.

3. The apparatus according to claim 1 further comprising an elastic diaphragm captured between said base and cap portions separating said acoustic transducer from said coupling chamber.

4. The apparatus according to claim 1 wherein said mouthpiece includes at least one tube forming said breathing passage.

5. The apparatus according to claim 4 wherein said breathing passage includes a plurality of tubular passages.

6. The apparatus according to claim 1 wherein said cap portion has a central aperture therethrough, and said mouthpiece is formed by an annular sleeve portion of said cap portion around said central aperture.

7. The apparatus according to claim 1 wherein said base portion has a tubular side wall and a disk shaped bottom closing one end of said tubular side wall, said tubular side wall having an opposite end adapted to telescopically engage an end portion of said cap portion.

8. The apparatus according to claim 1 further comprising an elastic diaphragm sandwiched between said cap portion and said base portion to prevent contamination of said transducer and said audio generator in said base portion through said coupling chamber.

9. The apparatus according to claim 1 wherein said cap portion includes said transducer and an elastic diaphragm between said transducer and said chamber.

10. The apparatus according to claim 9 wherein said base portion is separate from said cap portion and said base portion contains said audio generator and said base portion is connected to said cap portion by wires connecting said audio generator to said acoustic transducer.

11. The apparatus according to claim 10 wherein said housing further comprises a power supply in said base portion connected to said audio generator.

12. An apparatus for assisting a user in loosening phlegm and mucus plugs accumulated in a user's airways including bronchial tubes and lungs comprising:

a hollow housing having a cap portion forming at least part of an acoustic coupling chamber, said cap portion including a mouthpiece around a portion of said chamber having at least one breathing passage therethrough leading out of said cap portion, said mouthpiece including a connection for directing a pharmaceutical material into said breathing passage from a pharmaceutical delivery device;

an audio signal generator within a base portion of said housing having an acoustic transducer coupled to said chamber in said cap portion, said generator transmitting an acoustic waveform into said coupling chamber; and said mouthpiece coupling the acoustic coupling chamber into the user's airways when the mouthpiece is held in a user's mouth and permitting a patient to breathe through the breathing passage while said coupling chamber directs said acoustic waveform from said acoustic transducer into such a patient's airways.

13. An apparatus for assisting a patient in loosening phlegm and mucus collected in a patient's lungs, bronchial and/or tracheal passages comprising:

a cap portion module and a base portion module, said cap portion module forming at least part of an acoustic coupling chamber, said cap portion module including a mouthpiece around a portion of said chamber having at least one breathing passage therethrough leading out of said cap portion;

an audio signal generator housed within said base portion module coupled to an acoustic transducer in said cap portion module, said acoustic transducer transmitting an audio waveform into said coupling chamber; and said mouthpiece coupling the acoustic coupling chamber into a patient's airways when the mouthpiece is held in a patient's mouth and permitting a patient to breathe through the breathing passage while said coupling chamber directs said acoustic waveform from said acoustic transducer into such a patient's airways.

14. The apparatus according to claim 13 wherein the base portion module includes a power supply and said audio signal generator.

15. The apparatus according to claim 13 wherein said acoustic transducer is separated from said chamber by a flexible diaphragm.

16. The apparatus according to claim 13 wherein said base portion and said cap portion are connected by wires from said audio generator to said acoustic transducer.

17. The apparatus according to claim 13 wherein said mouthpiece includes a connection for receiving a pharmaceutical dispensing device.

18. The apparatus according to claim 17 wherein said connection connects a pharmaceutical dispensing device into said breathing passage.

19. The apparatus according to claim 18 wherein said acoustic generator includes a microphone for receiving acoustic signals through said coupling chamber from such a patient's airways.

20. The apparatus according to claim 19 further comprising a feedback control connected to said microphone and to said audio generator for controlling the frequency of said acoustic waveforms.

21. An apparatus for assisting a patient in loosening phlegm and mucus collected in a patient's lungs, bronchial and/or tracheal passages comprising:

a cap portion module and a base portion module, said cap portion module forming at least part of an acoustic coupling chamber, said cap portion module including a generally cup shaped face mask adapted to fit over a patient's nose and mouth to couple said chamber into a patient's airways, an audio signal generator housed within said base portion module and coupled to an acoustic transducer in said cap portion module, said acoustic transducer transmitting an acoustic waveform into said coupling chamber; and said face mask permitting a patient to breathe through said mask while said coupling chamber directs said acoustic waveform from said acoustic transducer into such a patient's airways.

22. The apparatus according to claim 21 wherein the base portion module includes a power supply and said audio signal generator.

23. The apparatus according to claim 21 wherein said acoustic transducer is separated from said chamber by a flexible diaphragm.

24. The apparatus according to claim 21 wherein said base portion and said cap portion are connected by wires from said audio generator to said acoustic transducer.

25. The apparatus according to claim 21 wherein said face mask includes a connection for receiving medication.

26. The apparatus according to claim 25 wherein said face mask includes an opening for removing expelled phlegm and mucus.

27. The apparatus according to claim 25 wherein said acoustic generator includes a microphone for receiving acoustic signals through said coupling chamber from such a patient's airways.

28. The apparatus according to claim 27 further comprising a feedback control connected to said microphone and to said audio generator for controlling the frequency of said acoustic waveforms.

29. The apparatus according to claim 21 wherein said face mask includes a plurality of straps for attachment to a patient's head.

* * * * *